(12) United States Patent
McCracken, Jr. et al.

(10) Patent No.: US 11,576,840 B1
(45) Date of Patent: *Feb. 14, 2023

(54) MEDICATION INVENTORY SYSTEM INCLUDING RFID BASED MEDICATION DISCREPANCY DETERMINATION AND RELATED METHODS

(71) Applicant: INMAR RX SOLUTIONS, INC., Ft. Worth, TX (US)

(72) Inventors: James W. McCracken, Jr., Winston Salem, NC (US); Brian Rogers, Greensboro, NC (US); Michael Snellenburg, Winston Salem, NC (US)

(73) Assignee: INMAR RX SOLUTIONS, INC., Ft. Worth, TX (US)

( * ) Notice: Subject to any disclaimer, the term of this patent is extended or adjusted under 35 U.S.C. 154(b) by 339 days.

This patent is subject to a terminal disclaimer.

(21) Appl. No.: 16/395,353

(22) Filed: Apr. 26, 2019

(51) Int. Cl.
| | |
|---|---|
| *G16H 20/10* | (2018.01) |
| *G16H 40/20* | (2018.01) |
| *G06Q 10/08* | (2012.01) |
| *A61J 7/00* | (2006.01) |

(Continued)

(52) U.S. Cl.
CPC ............ *A61J 7/0069* (2013.01); *G16H 20/10* (2018.01); *A61J 7/02* (2013.01); *A61J 2205/10* (2013.01); *A61J 2205/60* (2013.01); *G06Q 10/087* (2013.01); *G16H 40/20* (2018.01)

(58) Field of Classification Search
CPC .... A61J 7/0069; A61J 2205/60; G16H 20/10; G16H 40/20; G06Q 10/087
See application file for complete search history.

(56) References Cited

U.S. PATENT DOCUMENTS

| | | |
|---|---|---|
| 7,080,755 B2 | 7/2006 | Handfield et al. |
| 7,689,318 B2 | 3/2010 | Draper |
| 3,009,913 A1 | 8/2011 | Greyshock |

(Continued)

OTHER PUBLICATIONS

Murtadha et al., A Review of Medication Adherence Monitoring Technologies, MDPI. Applied System Innovation, May 6, 2018.*

(Continued)

*Primary Examiner* — Jay M. Patel
(74) *Attorney, Agent, or Firm* — Allen, Dyer, Doppelt + Gilchrist, P.A.

(57) ABSTRACT

A medication inventory system may include a medication tray that includes partitions defining compartments. The medication tray has a tray identifier associated therewith, and each compartment is for storing a respective medication having a radio frequency identification (RFID) tag associated therewith. The system may include an RFID tag reader, and a processor and an associated memory configured to maintain in the memory a desired respective medication within each compartment based upon the tray identifier, and cooperate with the RFID tag reader to determine the respective medication within each compartment based upon the respective RFID tag. The processor and associated memory may also be configured to determine a discrepancy between the determined medication within each compartment and the desired respective medication within each compartment, and when so generate a display notification that includes a visual indicator corresponding to each compartment determined to have the discrepancy.

13 Claims, 10 Drawing Sheets

(51) Int. Cl.
*A61J 7/02* (2006.01)
*G06Q 10/087* (2023.01)

(56) References Cited

U.S. PATENT DOCUMENTS

| | | | | |
|---|---|---|---|---|
| 8,046,242 B1* | 10/2011 | daCosta | ............... | G16H 10/60 600/300 |
| 8,065,035 B2 | 11/2011 | Ross et al. | | |
| 2001/0056358 A1* | 12/2001 | Dulong | ............... | G16H 20/10 705/2 |
| 2002/0040282 A1* | 4/2002 | Bailey | ............... | G16H 50/20 702/188 |
| 2004/0046020 A1* | 3/2004 | Andreasson | ............... | A61J 1/14 235/385 |
| 2007/0016443 A1* | 1/2007 | Wachman | ............... | G16H 20/10 600/300 |
| 2008/0035234 A1* | 2/2008 | Khan | ............... | B65B 3/003 700/231 |
| 2009/0138122 A1* | 5/2009 | Wagner | ............... | G07F 17/0092 700/226 |
| 2009/0232804 A1* | 9/2009 | Lazarides | ............... | A61P 7/06 435/69.6 |
| 2010/0324936 A1* | 12/2010 | Vishnubhatla | ............... | G06Q 40/08 715/810 |
| 2011/0240729 A1* | 10/2011 | Schuck | ............... | G16H 40/20 235/375 |
| 2011/0246219 A1 | 10/2011 | Smith et al. | | |
| 2014/0244296 A1* | 8/2014 | Linn | ............... | G16H 10/60 705/3 |
| 2014/0288952 A1* | 9/2014 | Smith | ............... | G06Q 40/08 705/2 |
| 2014/0335082 A1* | 11/2014 | Dransfield | ............... | A61K 31/337 424/133.1 |
| 2015/0093328 A1* | 4/2015 | Drummond | ............... | A61K 51/0478 534/10 |
| 2015/0151051 A1 | 6/2015 | Tsoukalis | | |
| 2015/0161558 A1* | 6/2015 | Gitchell | ............... | G06Q 50/22 235/375 |
| 2016/0364686 A1* | 12/2016 | Wolfe | ............... | G07F 17/0092 |
| 2017/0135907 A1* | 5/2017 | Paz | ............... | A61J 1/03 |
| 2017/0246083 A1 | 8/2017 | Amano et al. | | |
| 2017/0286903 A1* | 10/2017 | Elizondo, II | ............... | G06K 7/1413 |
| 2018/0260665 A1 | 9/2018 | Zhang et al. | | |
| 2018/0308571 A1* | 10/2018 | Tupler | ............... | A61J 7/0454 |
| 2019/0080790 A1* | 3/2019 | Patel | ............... | B65B 35/32 |
| 2019/0244699 A1* | 8/2019 | Loebig | ............... | G06N 20/20 |
| 2019/0333008 A1* | 10/2019 | Wolfe | ............... | G07F 17/0092 |
| 2020/0402632 A1* | 12/2020 | Van Schelven | ............... | G06Q 10/30 |

OTHER PUBLICATIONS

McCracken, Jr. et al., U.S. Appl. No. 16/395,343, filed Apr. 26, 2019.
Rogers et al., U.S. Appl. No. 16/704,573, filed Dec. 5, 2019.

* cited by examiner

MEDICATION INVENTORY SYSTEM INCLUDING RFID BASED MEDICATION DISCREPANCY DETERMINATION AND RELATED METHODS

TECHNICAL FIELD

The present invention relates to the field of medicine, and more particularly, to medication inventory systems and related methods.

BACKGROUND

Medications, including controlled substances, medical devices, and/or medical tools may be relatively important for treatment of a patient. Thus, it may be desirable to maintain medications in a relatively orderly and predictable fashion to reduce the amount of time it takes to access these medications, particularly in a time sensitive situation.

A medication tray is often used to provide a specific selection and quantity of medications for a particular medical use case, physician preference, and/or location. A given health care facility may have multiple variations of medication trays in use, each varying in type, amount, and/or placement of medications within the medication tray. Multiple medication trays may be used within a crash cart, which is a wheeled cart for dispensing of medication (e.g., in an emergency). Consequently, health care facilities may process and manage a relatively large quantity of medication trays used throughout a facility.

Accordingly, the medication trays are typically managed. Contents of the medication trays may be replenished and verified, for example, between uses. The verification may be performed manually and include inspection for recalled, expired, and misplaced medications.

U.S. Patent Application Publication No. 2014/0288952 to Smith et al. is directed to a system and method for tracking medical device inventory. More particularly, Smith et al. discloses trays that include implants and/or instruments, with each tray having a unique alphanumeric identifier (e.g., barcode) for inventory purposes, and each lot having a unique lot number. Each tray has an arrangement of implants or instruments predetermined by the manufacturer.

SUMMARY

A medication inventory system may include a medication tray that includes a plurality of partitions defining a plurality of compartments. The medication tray may have a tray identifier associated therewith. Each compartment may be for storing a respective medication having a radio frequency identification (RFID) tag associated therewith. The medication inventory system may include at least one RFID tag reader, and a processor and an associated memory configured to maintain in the memory a desired respective medication within each compartment based upon the tray identifier. The processor and associated memory may also be configured to cooperate with the at least one RFID tag reader to determine the respective medication within each compartment based upon the respective RFID tag, and determine a discrepancy between the determined medication within each compartment and the desired respective medication within each compartment, and when so generate a display notification that includes a visual indicator corresponding to each compartment determined to have the discrepancy.

The at least one RFID tag reader may include a plurality of RFID tag readers. The processor and associated memory may be configured to determine the respective medication in each compartment based upon a triangulation of the respective RFID tag from the plurality of RFID tag readers, for example. The processor and associated memory may be configured to determine the respective medication in each compartment based upon a time difference of arrival of radio frequency (RF) signals associated with the respective RFID tag to the plurality of RFID tag readers, for example.

The tray may include a floor and at least one sidewall extending from the floor. The at least one RFID tag reader may be carried by the floor, for example.

The system may include a display coupled to the processor for displaying the display notification. The display notification may include an image of the medication tray with the corresponding visual indicators overlaid thereon, for example.

The display notification may include a further visual indicator corresponding to each compartment determined to not have a discrepancy. The further visual indicator and visual indicator may have different visual characteristics, for example. The visual indicator may include one of a text indicator and a color indicator, for example.

The processor may be configured to determine whether the respective medication within each compartment has expired based upon the respective RFID tag, and when so, generate an expired medication display notification that includes an expired medication visual indicator corresponding to each compartment determined to have expired medication. The processor may be configured to determine whether the respective medication within each compartment has been recalled based upon the respective RFID tag, and when so, generate a recalled medication display notification that includes a recalled medication visual indicator corresponding to each compartment determined to have recalled medication, for example.

A method aspect is directed to a method of managing medication inventory in a medication inventory system that includes a medication tray including a plurality of partitions defining a plurality of compartments. The medication tray has a tray identifier associated therewith, and each compartment is for storing a respective medication having a radio frequency identification (RFID) tag associated therewith. The method may include using a processor and an associated memory to maintain in the memory a desired respective medication within each compartment based upon the tray identifier, and cooperate with at least one RFID tag reader to determine the respective medication within each compartment based upon the respective RFID tag. The method may also include using the processor and associated memory to determine a discrepancy between the determined medication within each compartment and the desired respective medication within each compartment, and when so generate a display notification that includes a visual indicator corresponding to each compartment determined to have the discrepancy.

A computer readable medium aspect is directed to a non-transitory computer readable medium for managing medication inventory in a medication inventory system that includes a medication tray including a plurality of partitions defining a plurality of compartments. The medication tray has a tray identifier associated therewith, and each compartment is for storing a respective medication having a radio frequency identification (RFID) tag associated therewith. The non-transitory computer readable medium includes computer executable instructions that when executed by a processor and associated memory cause the processor to perform operations. The operations may include maintaining in the memory a desired respective medication within each compartment based upon the tray identifier and cooperating with at least one RFID tag reader to determine the respective medication within each compartment based upon the respective RFID tag. The operations may also include determining a discrepancy between the determined medication within each compartment and the desired respective medication within each compartment, and when so generating a display notification that includes a visual indicator corresponding to each compartment determined to have the discrepancy.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime notation is used to indicate similar elements in alternative embodiments.

Figure 1:
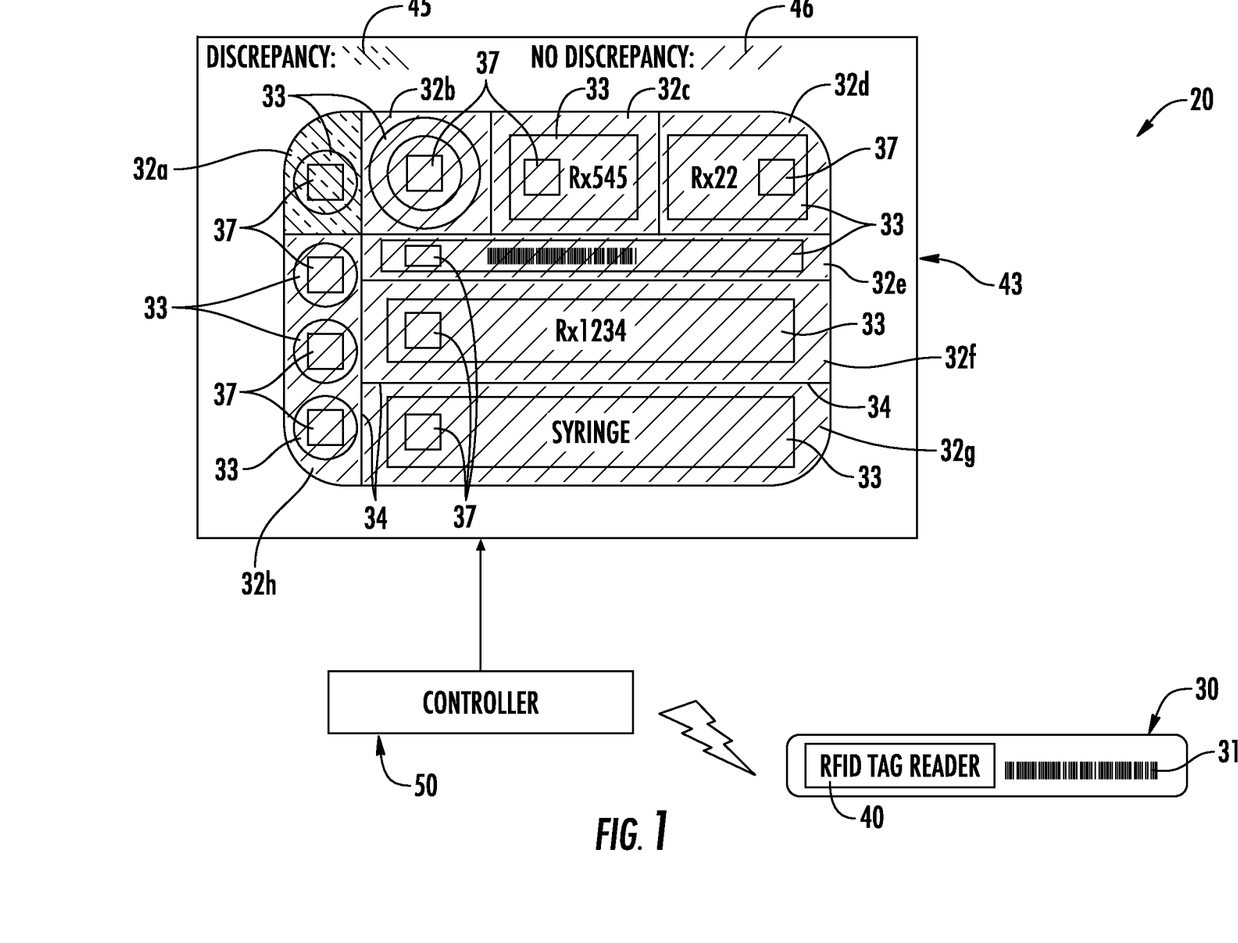
FIG. 1 is a schematic diagram of a medication inventory system in accordance with an embodiment.
Figure 2:
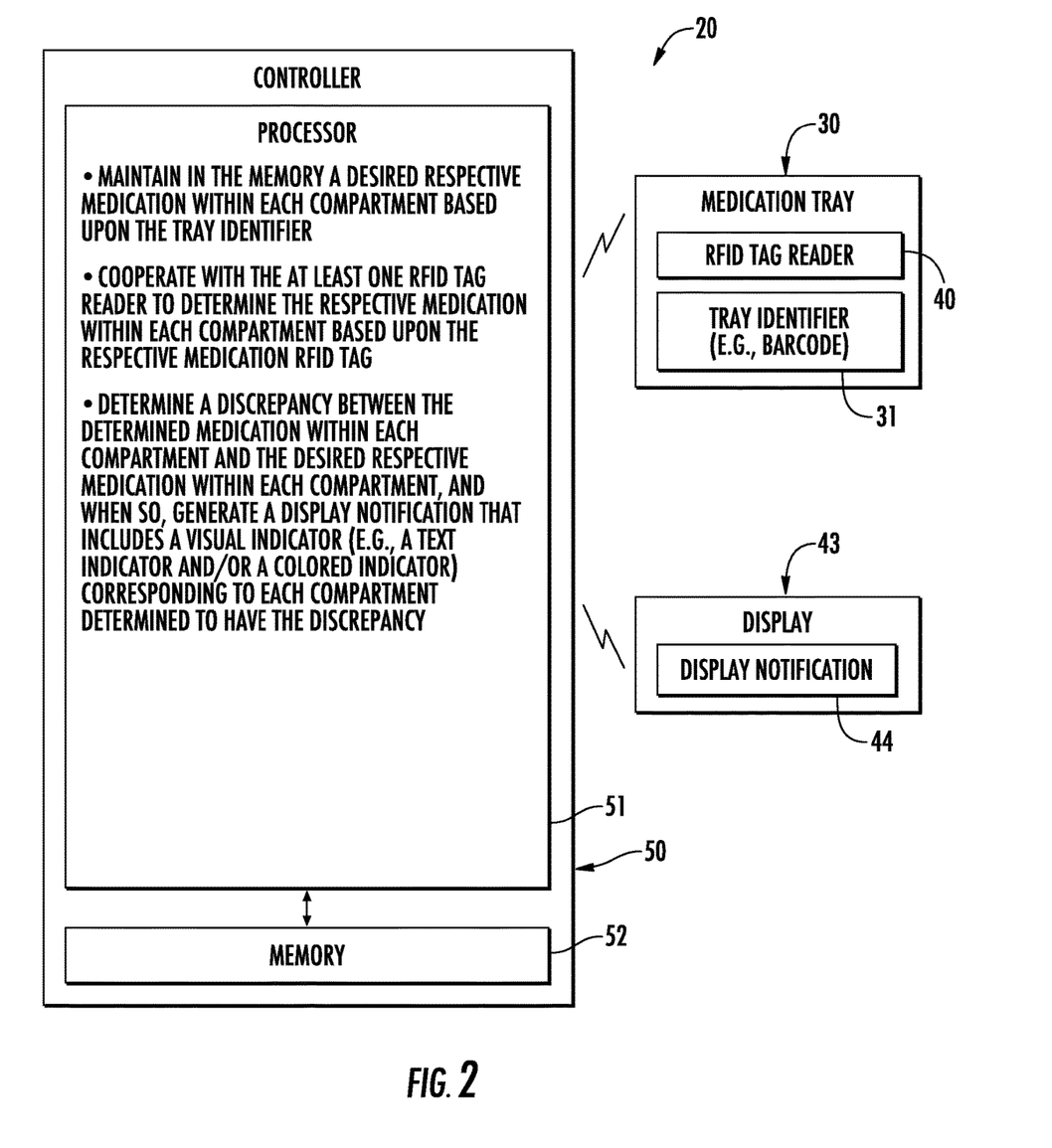
FIG. 2 is a schematic block diagram of the system of FIG. 1.
Figure 3:
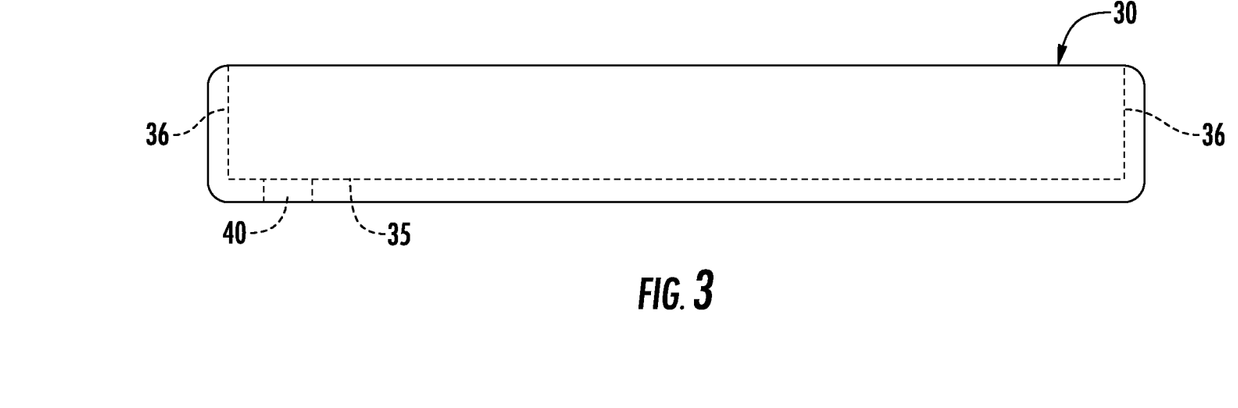
FIG. 3 is a more detailed schematic diagram of a medication tray of the medication inventory system of FIG. 1.

Referring initially to FIGS. 1-3, a medication inventory system 20 illustratively includes a medication tray 30. The medication tray 30 includes partitions 34 that define compartments 32a-32h. Each compartment may store a medication 33, multiple medications, a medical or medicated device, a medication container that includes individual medications therein, or other item or substance used for medical treatment. For example, the medication tray 30 may be part of a crash cart, as will be appreciated by those skilled in the art. Of course, the medication tray 30 may be used in other medical environments, for example, an examination room, emergency room, treatment room, operating room, etc.

Each medication 33, and more particularly, each medication container, has a radio frequency identification tag (RFID) tag 37 associated therewith. Each RFID tag 37 identifies the medication 33, for example, by name, type, quantity, dosage, lot number, expiration date, etc.

The medication tray 30 has a tray identifier 31 associated therewith. The tray identifier 31 may be in the form of a barcode, for example, that may be printed or applied (e.g., via an adhesive label) on the medication tray 30. The tray identifier 31 may be in the form of another type of identifier, for example, a quick-response (QR) code, alphanumeric characters, or other optically recognizable and unique code. The tray identifier 31 may also be in the form of an RFID tag.

The medication inventory system 20 also includes a RFID tag reader 40 carried by the medication tray 30. For example, the medication tray 30 includes a floor 35 and sidewalls 36 extending upwardly from the floor. The RFID tag reader 40 may be carried by the floor, for example, or coupled to or affixed to the floor via an adhesive material layer. The RFID tag reader 40 may alternatively be embedded within the floor 35. In some embodiments, the RFID tag reader 40 may be carried by one or more of the sidewalls 36. In other embodiments, the RFID tag reader 40 may be embodied in a mobile electronic device, for example, a handheld RFID tag scanner.

The medication inventory system 20 includes a controller 50. The controller 50 includes a processor 51 and an associated memory 52. The controller 50 may be carried by medication tray 30 or by a housing of a remote device, for example, that is coupled (e.g., wirelessly) to the RFID tag reader 40. The controller 50 may be in a cloud computing environment, for example.

A display 43 is coupled to the controller 50. The display 43 may be adjacent the medication tray 30 or may be remote, for example, a remote display and/or a display of a mobile wireless communications device, such as, for example, a mobile telephone or tablet computer. In some embodiments, the controller 50 may be carried within the housing of the display 43 or within the same housing of the display, for example, in a housing of a mobile wireless communications device or tablet computer.

Figure 4:
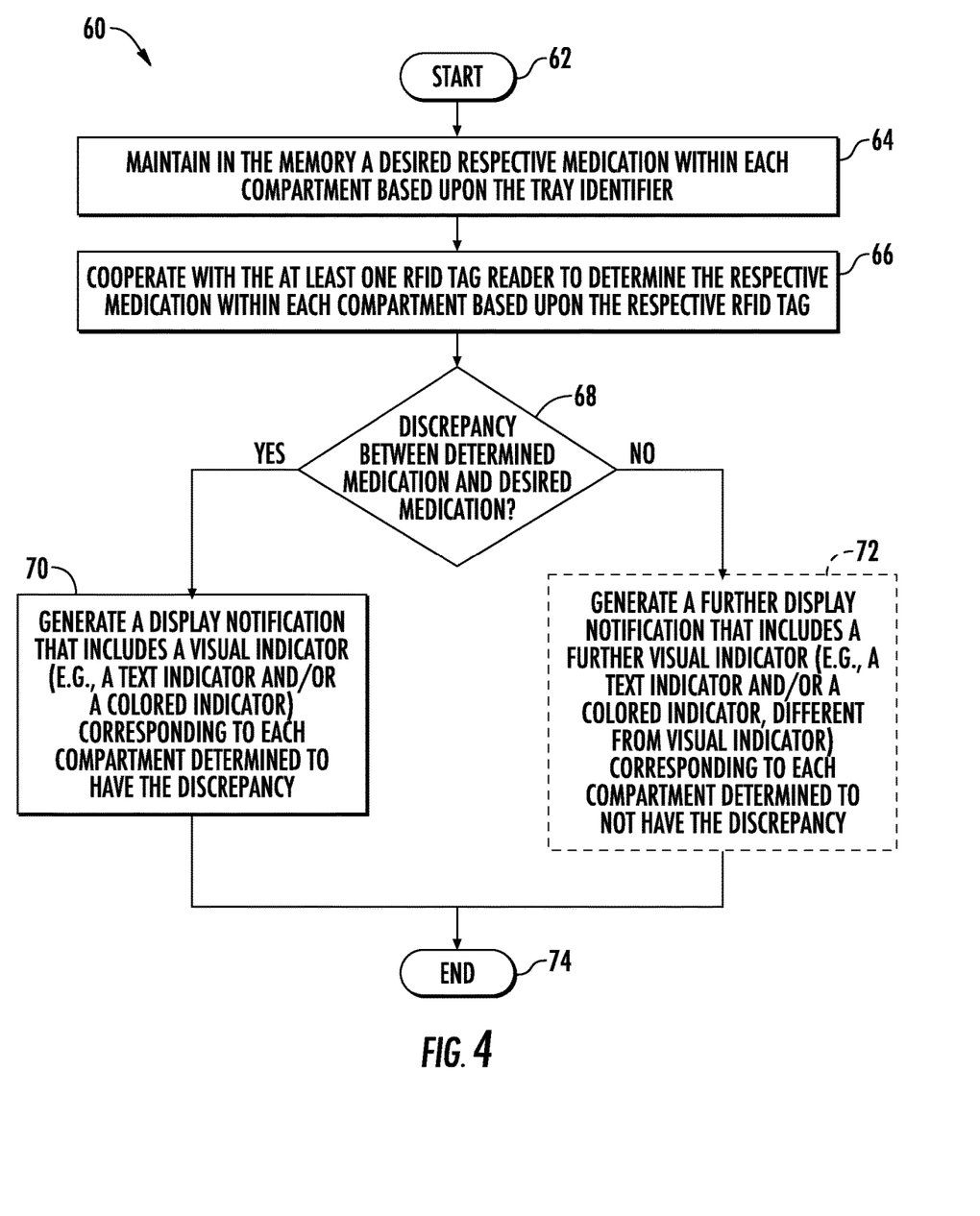
FIG. 4 is a flow diagram illustrating operation of the controller of the medication inventory system of FIG. 1.

Referring now to the flowchart 60 in FIG. 4, beginning at Block 62, operations of the medication inventory system 20 will now be described with respect to operations of the controller 50. While operations will be described herein with respect to the controller 50, the operations are performed through cooperation between the processor 51 and the memory 52. At Block 64, the controller 50 maintains, in the memory 52, a desired respective medication within each compartment 32a-32h based upon the tray identifier 31. More particularly, the memory 52 includes a reference, mapping, or configurations of which medications are desired or expected within each of the compartments 32a-32h for the given tray 30 associated with the tray identifier 31. As will be appreciated by those skilled in the art, a different configuration or expected medication may be within each compartment for different tray identifiers.

The controller 50 may obtain the tray identifier 31 by manual entry, through cooperation with an optical scanner or optical imaging device, or through cooperation with the RFID tag reader 40. The controller 50 cooperates to identify the particular medication tray 30 based upon the tray identifier 31.

The controller 50, at Block 66, cooperates with the RFID tag reader 40 to determine the respective medication 33 within each compartment 32a-32h based upon the respective RFID tag 37.

The controller 50 determines whether there is a discrepancy between the determined medication 33 within each compartment 32a-32h and the desired respective medication within each compartment (Block 68). In particular, the determined medication 33 within each compartment 32a-32h is compared or matched to the desired respective medication stored in the memory 52. Those skilled in the art will appreciate that the identifying data from the medication determination may be matched to corresponding stored desired medication data stored in the memory 52. In some embodiments, a discrepancy may be determined when a threshold amount of matched data is not exceeded. In other words, if the controller 50 cannot determine within a threshold amount of certainty, for example, less than 100%, that the determined medication 33 matches the expected medication for a given compartment, the controller may determine that there is a discrepancy. In other words, a mismatch of medication 33 may be determined.

If at Block 68 it is determined that there is discrepancy between the determined medication within each compartment 32a-32h and the desired respective medication with each compartment, the controller 50 generates a display notification 44 that includes a visual indicator 45 corresponding to each compartment determined to have a discrepancy (Block 70). The display notification 44 may include an image of the medication tray 30 with the corresponding visual indicators 45 overlaid thereon. The display notification 44 may, in some embodiments, also include further visual indicators 46 having one or more different visual characteristics that correspond to each compartment 32a-32h that does not have a discrepancy (Block 72). The visual indicators 45 may be in the form of a text indictor (e.g., "OK", or "DISCREPANCY") and/or a color indictor (e.g., a red box overlaid corresponding compartments having a discrepancy and a green box overlaid corresponding compartments not having a discrepancy). Upon a discrepancy, the controller 50 may display or provide an indication of the expected medication, and in some instances recommend a substitute medication (e.g., a generic or similarly performing). Operations end at Block 74. Of course, in some embodiments, if there are no discrepancies, no display notification may be displayed and the operations may end at Block 74.

Figure 5:
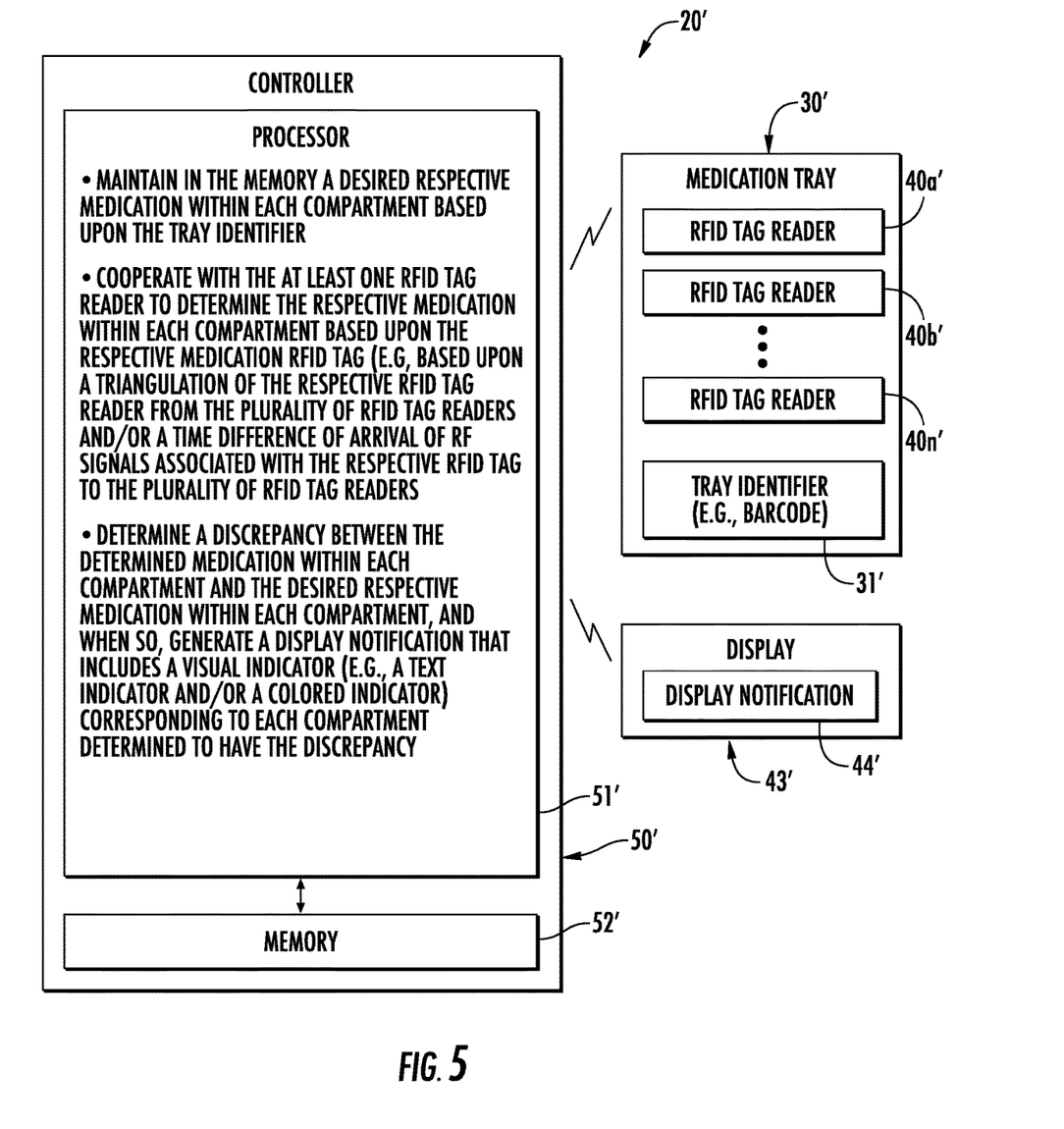
FIG. 5 is a schematic diagram of a medication inventory system in accordance with another embodiment.
Figure 6:
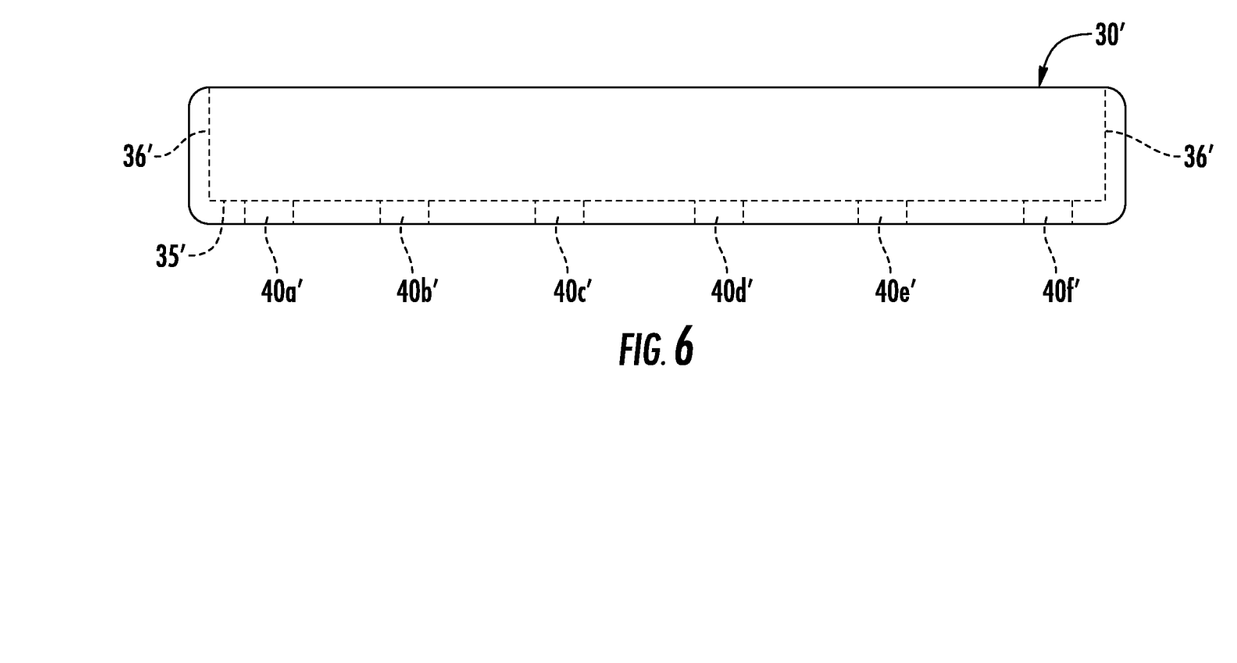
FIG. 6 is a schematic diagram of a medication tray of a medication inventory system in accordance with the medication inventory system of FIG. 5.

Referring now to FIGS. 5 and 6, in another embodiment, the medication inventory system 20' may include more than one RFID tag reader 40a'-40n'. For example, the RFID tag readers 40a'-40n' may be spaced apart in an array carried by the floor 35' of the medication tray 30' or embedded within the floor of the medication tray. While several RFID tag readers 40a'-40n' are illustrated, those skilled in the art will appreciate that there may be any number RFID tag readers. The controller 50' may determine the respective medication in each compartment based upon a triangulation of the respective RFID tag 37' from the RFID tag readers 40a-40n', and more particularly, based upon adjacent ones of the RFID tag readers. The controller 50' may alternatively or additionally determine the respective medication in each compartment based upon a time difference of arrival of RF signals associated with the respective RFID tag 37' to the RFID tag readers 40a'-40n'. Other and/or additional techniques may be used to determine the respective medication 33' in each compartment, as will be appreciated by those skilled in the art.

Figure 7:
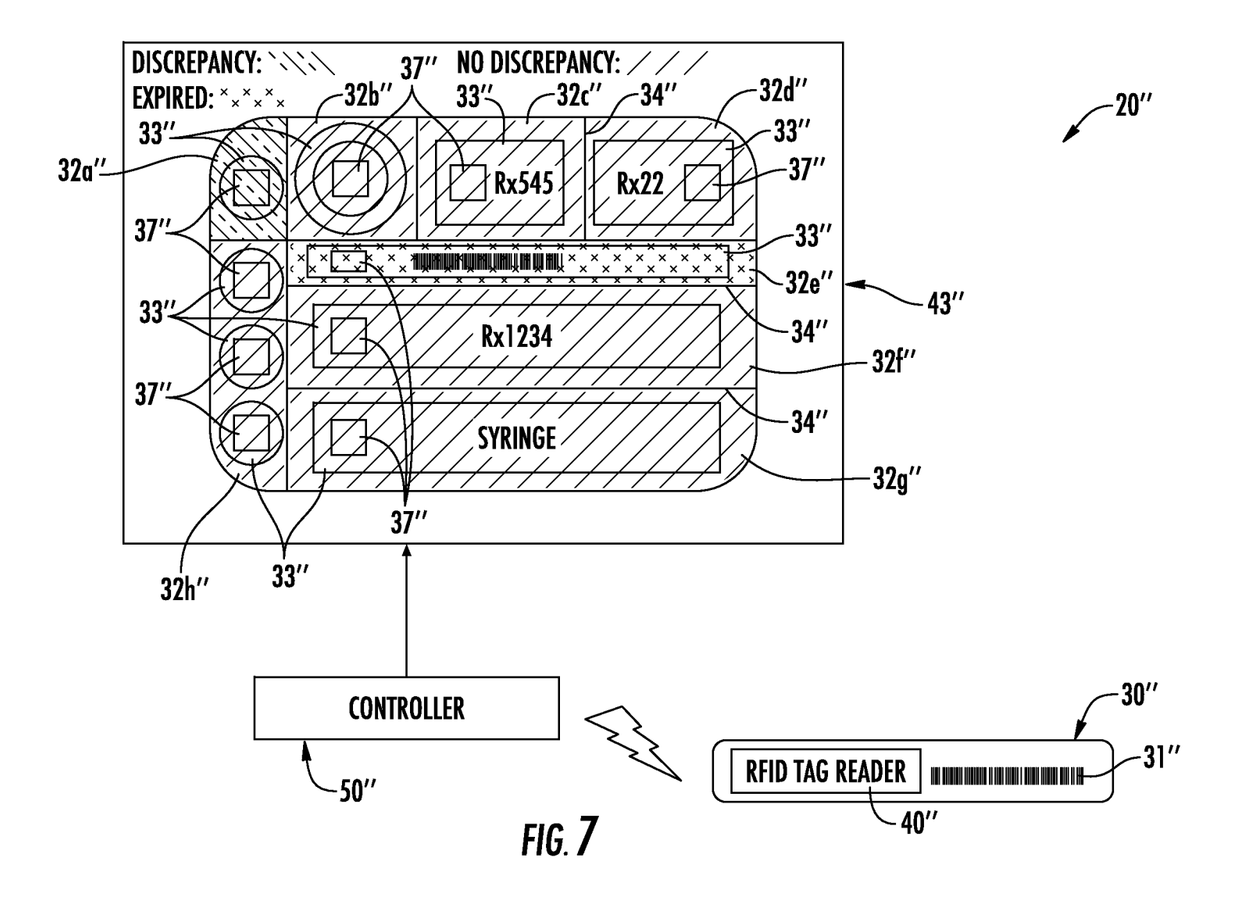
FIG. 7 is a schematic diagram of a medication inventory system in accordance with another embodiment.
Figure 8:
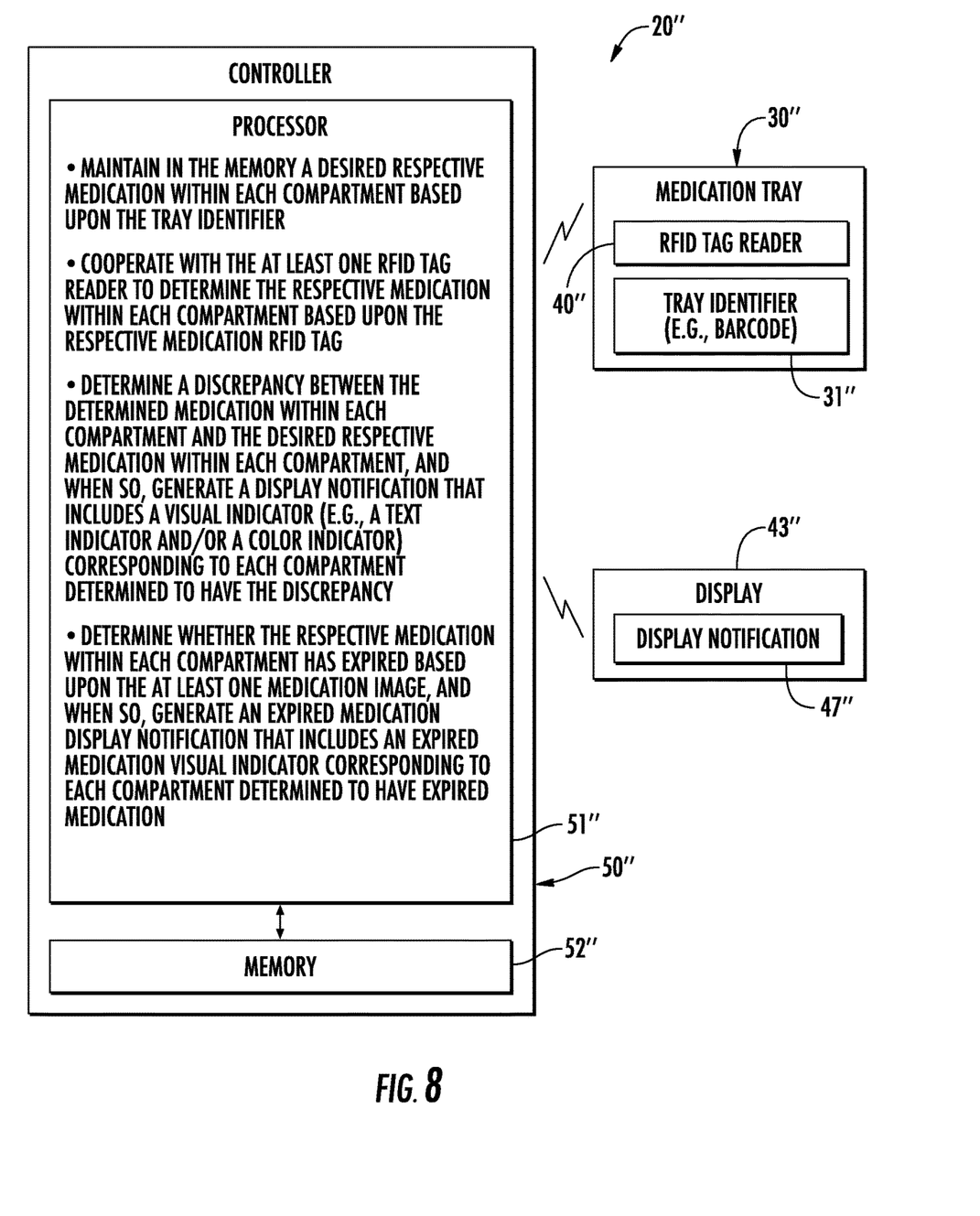
FIG. 8 is a schematic block diagram of the medication inventory system of FIG. 7.

Referring now to FIGS. 7 and 8, in another embodiment, the controller 50" determines whether the respective medication 33" within each compartment 32a"-32h" has expired based upon the respective RFID tag 37". When a respective medication 33" is determined to have expired, the controller 50" generates an expired medication display notification 47" that includes an expired medication visual indicator 48" corresponding to each compartment determined to have expired medication. The expired medication display notification 47" may be similar (e.g., color indicator and/or text) to the notification described above with respect a determined discrepancy, but may have different visual characteristics. In some embodiments, the expired medication visual indicator 48" may be integrated within the display notification 44" of a discrepancy. For example, the visual indicator 45" included within the display notification 44" may indicate the type of discrepancy by way of the visual characteristics (e.g., expired, not expected medication).

Figure 9:
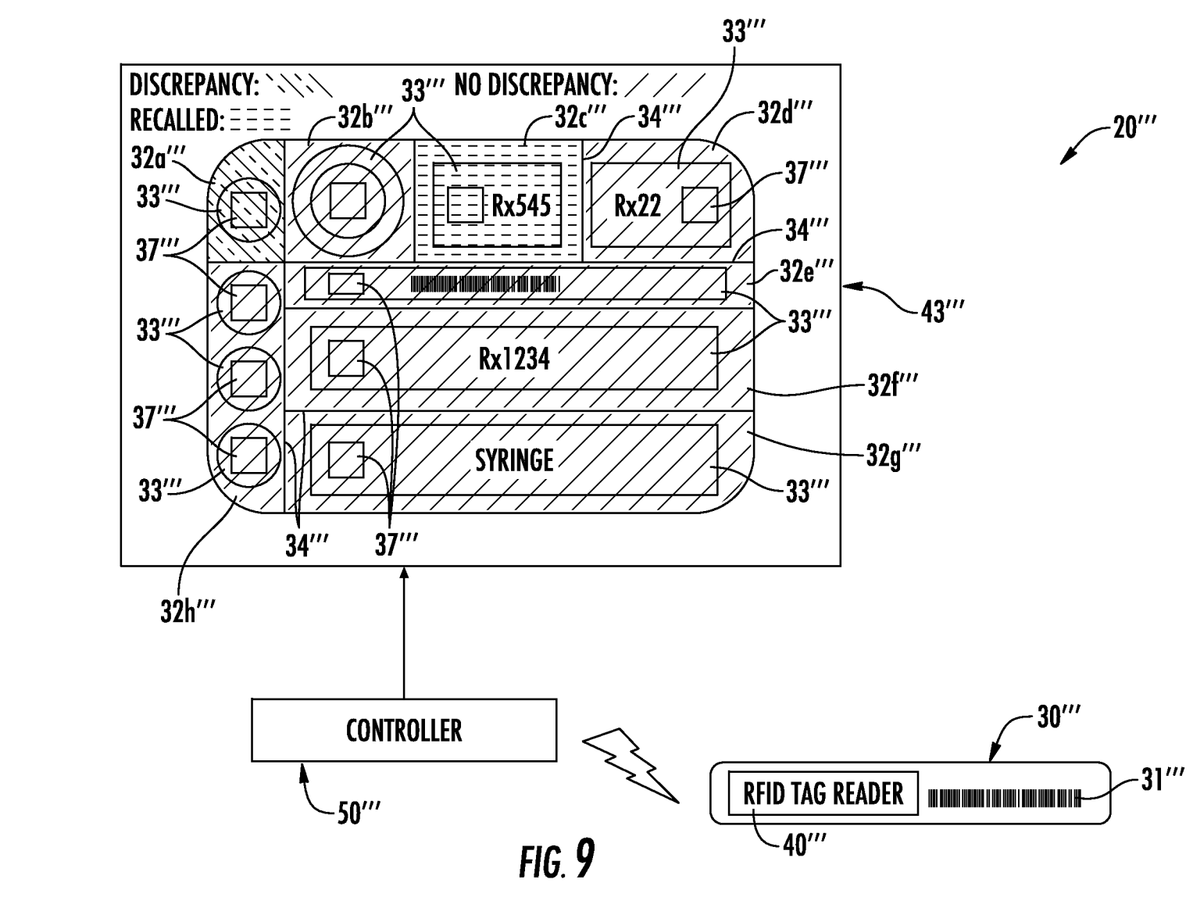
FIG. 9 is a schematic diagram of a medication inventory system in accordance with another embodiment.
Figure 10:
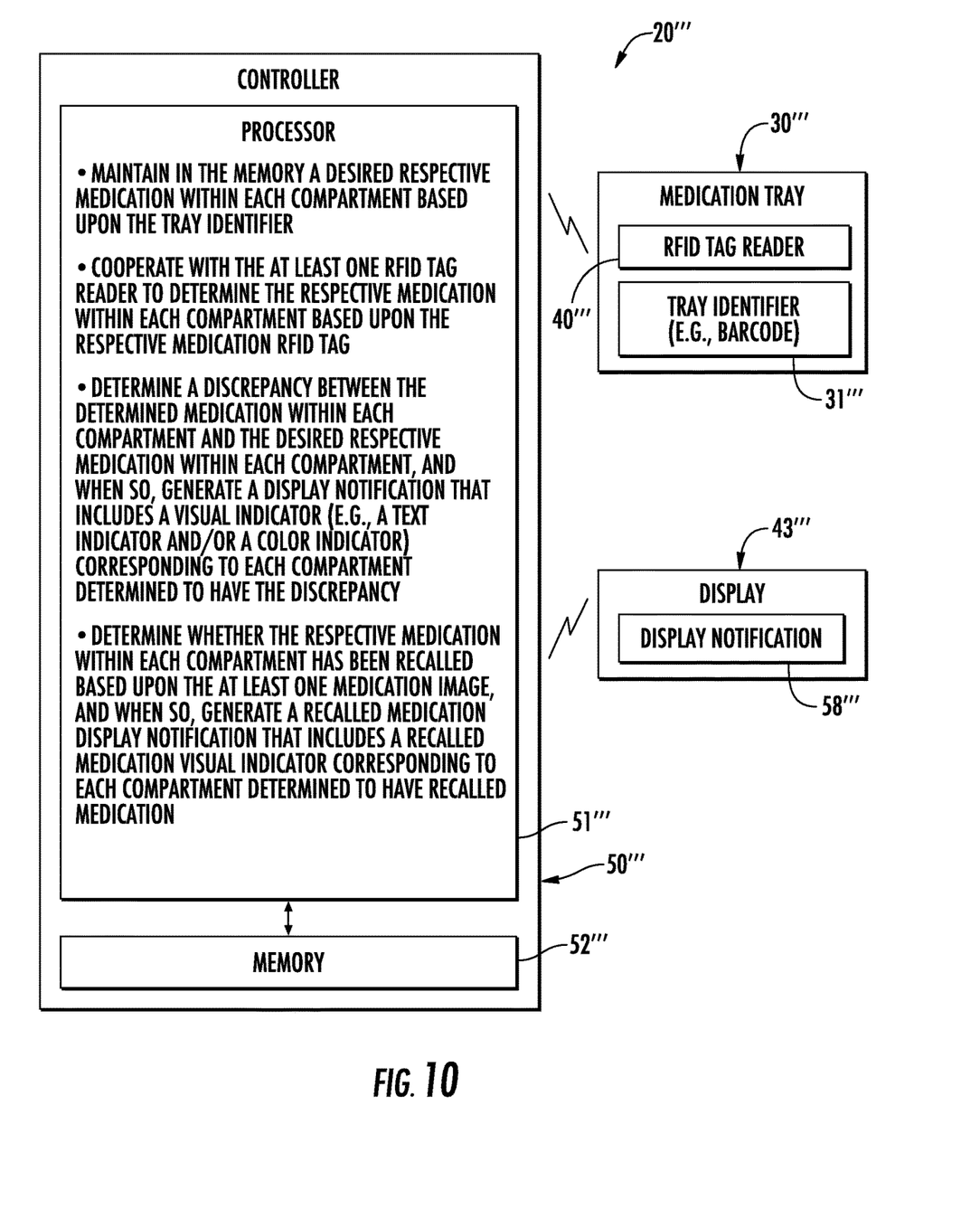
FIG. 10 is a schematic block diagram of the medication inventory system of FIG. 8.

Referring now to FIGS. 9 and 10, in another embodiment, the controller 50''' determines whether the respective medication within each compartment 32a'''-32h''' has been recalled based upon the respective RFID tag 37'''. When a respective medication 33''' is determined to have been recalled, the controller 50''' generates a recalled medication display notification 58''' that includes a recalled medication visual indicator 59''' corresponding to the each compartment 32a'''-32h''' determined to have recalled medication. The recalled medication display notification 58''' may be similar (e.g., color indicator and/or text) to the notification 44 described above with respect a determined discrepancy, but may have different visual characteristics. In some embodiments, the recalled medication visual indicator 59''' may be integrated within the display notification 44 and/or expired medication display notification 47". For example, the visual indicator included within the display notification 44 may indicate the type of discrepancy by way of the visual characteristics (e.g., recalled, not expected medication, expired).

The medication inventory system 20 may be advantageous for providing increased accuracy loading or packing of medication 33 within the compartments 32a-32h of a given medication tray 30. More particularly, the medication inventory system 20 described herein may be particularly advantageous for confirming medications 33 within a crash cart, which typically includes medications for emergency treatment. As will be appreciated by those skilled in the art, items within a crash cart are typically located in the same compartment within a tray among different crash carts within a given hospital or hospital system. Medical professionals may typically, in an emergency situation, reach for a medication 33 within a given compartment without inspection of the medication to confirm the accuracy of the medication within the compartment. Accordingly, a misplaced medication 33 or a discrepancy of what is expected within a compartment and what is actually within the compartment may have far reaching implications. The system 20 described herein may address these shortcomings by providing a mapping of medications 33 within the medication tray 30 and confirmation that the expected medications match the actual medications within a compartment, and by providing notification when there is a discrepancy.

A method aspect is directed to a method of managing medication inventory in a medication inventory system 20 that includes a medication tray 30 including a plurality of partitions 34 defining a plurality of compartments 32a-32h. The medication tray 30 has a tray identifier 31 associated therewith, and each compartment is for storing a respective medication 33 having a radio frequency identification (RFID) tag 37 associated therewith. The method includes using a processor 51 and an associated memory 52 to maintain in the memory a desired respective medication within each compartment 32a-32h based upon the tray identifier 31, and cooperate with at least one RFID tag reader 40 to determine the respective medication 33 within each compartment based upon the respective RFID tag 37. The method also includes using the processor 51 and associated memory 52 to determine a discrepancy between the determined medication 33 within each compartment and the desired respective medication within each compartment, and when so generate a display notification 44 that includes a visual indicator 45 corresponding to each compartment 32a-32h determined to have the discrepancy.

A computer readable medium aspect is directed to a non-transitory computer readable medium for managing medication inventory in a medication inventory system 20 that includes a medication tray 30 including a plurality of partitions 34 defining a plurality of compartments 32a-32h. The medication tray 30 has a tray identifier 31 associated therewith, and each compartment 32a-32h is for storing a respective medication 33 having a radio frequency identification (RFID) tag 37 associated therewith. The non-transitory computer readable medium includes computer executable instructions that when executed by a processor 51 and associated memory 52 cause the processor to perform operations. The operations include maintaining in the memory 52 a desired respective medication within each compartment 32a-32h based upon the tray identifier 31 and cooperating with at least one RFID tag reader 40 to determine the respective medication 33 within each compartment based upon the respective RFID tag 37. The operations also include determining a discrepancy between the determined medication 33 within each compartment 32a-32h and the desired respective medication within each compartment, and when so generating a display notification 44 that includes a visual indicator 45 corresponding to each compartment determined to have the discrepancy.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A medication inventory system comprising:
    a medication tray comprising a floor and at least one sidewall extending upwardly from the floor, and a plurality of partitions extending upwardly from the floor defining a plurality of compartments, the medication tray having a tray identifier associated therewith, each compartment for storing a respective medication, and each medication having a radio frequency identification (RFID) tag associated therewith;
    a plurality of RFID tag readers extending upwardly from the floor; and
    a processor and an associated memory configured to
        maintain in the memory a desired respective medication within each compartment based upon the tray identifier,
        cooperate with each RFID tag reader to determine the respective medication within each compartment based upon a triangulation of the respective RFID tag from the plurality of RFID tag readers, and
        determine a discrepancy between the determined medication within each compartment and the desired respective medication within each compartment, and when so generate a display notification that includes a visual indicator corresponding to each compartment determined to have the discrepancy.

2. The medication inventory system of claim 1 wherein the processor and associated memory are configured to determine the respective medication in each compartment based upon a time difference of arrival of radio frequency (RF) signals associated with the respective RFID tag to the plurality of RFID tag readers.

3. The medication inventory system of claim 1 comprising a display coupled to the processor for displaying the display notification; and wherein the display notification comprises an image of the medication tray with the corresponding visual indicators overlaid thereon.

4. The medication inventory system of claim 1 wherein the display notification comprises a further visual indicator corresponding to each compartment determined to not have a discrepancy; and wherein the further visual indicator and visual indicator have different visual characteristics.

5. The medication inventory system of claim 1 wherein the visual indicator comprises one of a text indicator and a color indicator.

6. The medication inventory system of claim 1 wherein said processor is configured to determine whether the respective medication within each compartment has expired based upon the respective RFID tag, and when so, generate an expired medication display notification that includes an expired medication visual indicator corresponding to each compartment determined to have expired medication.

7. The medication inventory system of claim 1 wherein said processor is configured to determine whether the respective medication within each compartment has been recalled based upon the respective RFID tag, and when so, generate a recalled medication display notification that includes a recalled medication visual indicator corresponding to each compartment determined to have recalled medication.

8. A medication inventory device for a medication inventory system comprising a medication tray comprising a floor and at least one sidewall extending upwardly from the floor, and a plurality of partitions extending upwardly from the floor defining a plurality of compartments, the medication tray having a tray identifier associated therewith, each compartment for storing a respective medication, and each medication having a radio frequency identification (RFID) tag associated therewith, the medication inventory device comprising:
    a plurality of RFID tag readers extending upwardly from the floor; and
    a processor and an associated memory configured to
        maintain in the memory a desired respective medication within each compartment based upon the tray identifier,
        cooperate with each RFID tag reader to determine the respective medication within each compartment based upon a triangulation of the respective RFID tag from the plurality of RFID tag readers, and
        determine a discrepancy between the determined medication within each compartment and the desired respective medication within each compartment, and when so generate a display notification that includes a visual indicator corresponding to each compartment determined to have the discrepancy.

9. The medication inventory device of claim 8 wherein the processor and associated memory are configured to determine the respective medication in each compartment based upon a time difference of arrival of radio frequency (RF) signals associated with the respective RFID tag to the plurality of RFID tag readers.

10. A method of managing medication inventory in a medication inventory system comprising a medication tray comprising a floor and at least one sidewall extending upwardly from the floor, and a plurality of partitions extending upwardly from the floor defining a plurality of compartments, the medication tray having a tray identifier associated therewith, each compartment for storing a respective medication, and each medication having a radio frequency identification (RFID) tag associated therewith, the method comprising:

using a processor and an associated memory to
maintain in the memory a desired respective medication within each compartment based upon the tray identifier,
cooperate with each of a plurality of RFID tag readers extending upwardly from the floor to determine the respective medication within each compartment based upon a triangulation of the respective RFID tag from the plurality of RFID tag readers, and
determine a discrepancy between the determined medication within each compartment and the desired respective medication within each compartment, and when so generate a display notification that includes a visual indicator corresponding to each compartment determined to have the discrepancy.

11. The method of claim 10 wherein using the processor and associated memory comprises using the processor and associated memory to determine the respective medication in each compartment based upon a time difference of arrival of radio frequency (RF) signals associated with the respective RFID tag to the plurality of RFID tag readers.

12. A non-transitory computer readable medium for managing medication inventory in a medication inventory system comprising a medication tray comprising a floor and at least one sidewall extending upwardly from the floor, and a plurality of partitions extending upwardly from the floor defining a plurality of compartments, the medication tray having a tray identifier associated therewith, each compartment for storing a respective medication, and each medication having a radio frequency identification (RFID) tag associated therewith, the non-transitory computer readable medium comprising computer executable instructions that when executed by a processor and associated memory cause the processor to perform operations comprising:

maintaining in the memory a desired respective medication within each compartment based upon the tray identifier;
cooperating with each of a plurality of RFID tag readers extending upwardly from the floor to determine the respective medication within each compartment based upon a triangulation of the respective RFID tag from the plurality of RFID tag readers; and
determining a discrepancy between the determined medication within each compartment and the desired respective medication within each compartment, and when so generating a display notification that includes a visual indicator corresponding to each compartment determined to have the discrepancy.

13. The non-transitory computer readable medium of claim 12 wherein the operations comprise determining the respective medication in each compartment based upon a time difference of arrival of radio frequency (RF) signals associated with the respective RFID tag to the plurality of RFID tag readers.

* * * * *

UNITED STATES PATENT AND TRADEMARK OFFICE
CERTIFICATE OF CORRECTION

PATENT NO. : 11,576,840 B1  
APPLICATION NO. : 16/395353  
DATED : February 14, 2023  
INVENTOR(S) : McCracken, Jr. et al.

Page 1 of 1

It is certified that error appears in the above-identified patent and that said Letters Patent is hereby corrected as shown below:

On the Title Page

Column 2, item (56)  Delete: "3,009,913 A1 8/2011 Greyshock"  
Insert: --8,009,913 A1 8/2011 Greyshock--

Signed and Sealed this  
Fifteenth Day of August, 2023

Katherine Kelly Vidal  
*Director of the United States Patent and Trademark Office*